(12) United States Patent
Weiss et al.

(10) Patent No.: US 8,071,081 B2
(45) Date of Patent: Dec. 6, 2011

(54) REDUCTION OF AIRBORNE MALODORS USING HYDROGEN PEROXIDE AND A CATALYST-COATED MEDIA

(75) Inventors: Carl S. Weiss, Buffalo Grove, IL (US); Anthony J. Wagner, Buffalo Grove, IL (US); Wayne M. Rees, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 352 days.

(21) Appl. No.: 12/270,896

(22) Filed: Nov. 14, 2008

(65) Prior Publication Data

US 2009/0130047 A1    May 21, 2009

Related U.S. Application Data

(60) Provisional application No. 60/988,302, filed on Nov. 15, 2007.

(51) Int. Cl.
*A61L 9/015* (2006.01)
*A61L 9/00* (2006.01)
*A01N 59/16* (2006.01)
*A01N 25/00* (2006.01)
*A61K 33/24* (2006.01)

(52) U.S. Cl. .................... 424/76.2; 424/76.21; 424/405; 424/617

(58) Field of Classification Search .................... None
See application file for complete search history.

(56) References Cited

U.S. PATENT DOCUMENTS

| | | |
|---|---|---|
| 3,911,080 A | 10/1975 | Mehl et al. |
| 3,969,479 A | 7/1976 | Lonnes et al. |
| 4,975,254 A | 12/1990 | Svara et al. |
| 4,988,505 A | 1/1991 | Watanabe et al. |
| 5,009,869 A | 4/1991 | Weinburg et al. |
| 5,139,957 A | 8/1992 | Grack |
| 5,160,707 A | 11/1992 | Murray |
| 5,186,903 A | 2/1993 | Cornwell |
| 5,207,877 A | 5/1993 | Weinberg et al. |
| 5,399,319 A | 3/1995 | Schoenberger |
| 5,597,539 A | 1/1997 | Fakley et al. |
| 5,891,221 A | 4/1999 | Rohrbach et al. |
| 5,989,497 A | 11/1999 | Labonte, Jr. |
| 6,183,708 B1 | 2/2001 | Hei et al. |
| 6,197,288 B1 | 3/2001 | Mankoo |
| 6,277,344 B1 | 8/2001 | Hei et al. |
| 6,391,272 B1 | 5/2002 | Schroeder |
| 6,429,169 B1 | 8/2002 | Ichinose |
| 6,488,902 B1 | 12/2002 | DeCato et al. |
| 6,495,096 B1 | 12/2002 | Hamaguchi |
| 6,503,471 B1 | 1/2003 | Han et al. |
| 6,534,024 B2 | 3/2003 | Honjo et al. |
| 6,602,918 B1 | 8/2003 | Ichinose |
| 6,843,835 B2 | 1/2005 | Fornai et al. |
| 6,969,486 B1 | 11/2005 | Cooper et al. |
| 7,132,479 B2 | 11/2006 | Engelhardt et al. |
| 7,147,692 B2 | 12/2006 | Fornai et al. |
| 7,147,822 B2 | 12/2006 | Parkhurst et al. |
| 7,294,320 B2 | 11/2007 | Pettibone |
| 7,326,382 B2 | 2/2008 | Adiga et al. |
| 2004/0143133 A1 | 7/2004 | Smith et al. |
| 2004/0250683 A1 | 12/2004 | Soane et al. |
| 2005/0008608 A1 | 1/2005 | Parkhurst et al. |
| 2006/0006121 A1 | 1/2006 | Simpson et al. |
| 2006/0120913 A1 | 6/2006 | Wuest |
| 2006/0280665 A1 | 12/2006 | Rees et al. |

FOREIGN PATENT DOCUMENTS

| | | |
|---|---|---|
| EP | 0433564 A | 6/1991 |
| WO | 20030057262 A | 7/2003 |
| WO | 20060135620 A | 12/2006 |
| WO | 20070143455 A | 12/2007 |

OTHER PUBLICATIONS

Rohatgi et al. 2001 International Conference on Environmental Systems Orlando, Florida, USA; 7 pages.*
Database WPI Week 197121, Thomson Scientific, London, GB; AN; XP002515617; & SU 277 375 A (Analytical Instruments DE) Jul. 22, 1970; abstract.
PCT/US2008/012773 International Search Report and Search Opinion dated Feb. 25, 2009.

* cited by examiner

*Primary Examiner* — Ernst Arnold

(57) ABSTRACT

Compositions, methods and apparatuses for reducing or eliminating malodors from indoor air are described. The method utilizes vapor phase hydrogen peroxide (VPHP) generated from either evaporation from an aqueous-based liquid composition or sublimation from a solid hydrogen peroxide-containing compound. VPHP engages a media coated with at least one transitional metal element or compound, which acts as an oxidation catalyst, in the presence of air that contains malodorous compounds to provide increased efficacy of malodor molecule oxidation. The apparatus can employ a disposable porous non-woven filter pad coated with one or more transition metal compounds, and a solid source of VPHP. Malodor-containing air engages the pad in the presence of the VPHP to effectively oxidize the malodorants. The apparatus can also include a mechanism to provide color change(s) in the presence of VPHP to indicate whether the device contains VPHP or not.

23 Claims, 7 Drawing Sheets

REDUCTION OF AIRBORNE MALODORS USING HYDROGEN PEROXIDE AND A CATALYST-COATED MEDIA

CROSS-REFERENCE TO RELATED APPLICATION

This application is a non-provisional U.S. application which is based on and claims priority under 35 U.S.C. 119(e) from provisional Application Ser. No. 60/988,302, filed on Nov. 15, 2007.

BACKGROUND

1. Technical Field

This disclosure relates to odor reduction or elimination from air through the use of vapor phase hydrogen peroxide in combination with a media coated with a transition metal element or compound. Odor reduction or elimination is accomplished by the synergistic introduction of vapor phase hydrogen peroxide (VPHP) into malodorous air and allowing the malodorant and VPHP to engage a catalyst, where the catalyst comprises at least one transition metal element or compound.

2. Description of Related Art

The issue of malodors, and their potential adverse effects on health and quality of indoor life, has been a concern for centuries. While malodors are sometimes an indicator of danger or disease, they are typically little more than an unpleasant experience that negatively affect ambiance. Thus, for both nuisance and health reasons, methods have been sought to eliminate or substantially alleviate malodors wherever they are encountered, especially from indoor environments.

Many devices and techniques have evolved to treat malodors. Such methods or techniques have included masking odors with perfumes, fragrances or incense, displacing malodorous air with fans or blowers, absorbing malodors with activated carbon or other materials, and removing malodors from air using electrostatic precipitators. These methods and devices, though somewhat effective in lessening the impact of malodors, generally do not actually eliminate the malodorous substances themselves from the indoor environment.

While displacing malodorous indoor air with fans or blowers, and replacing it with fresh outdoor air may actually eliminate malodors from an indoor environment, such an approach to indoor malodor abatement is economically impractical when said indoor air is temperature and/or humidity controlled. Further, many indoor spaces such as high-rise apartments and high-rise offices do not have direct access to fresh outdoor air.

In the case of activated carbon, malodorous materials are not changed and may in fact be desorbed as a result of temperature fluctuations or interior carbon particle saturation—thus rendering this method less than optimally effective. The mechanism involved entails three separate (physical) processes which leave the malodorous substances intact: condensation, Van der Waals attraction and diffusion to the carbon particle interior.

Similarly, electrostatic precipitation consists essentially of a flocculation and subsequent collection of charged dust particles. Odor removal with this technique requires adsorption of malodors onto the targeted dust particles. Like techniques using activated carbon, this approach is clearly limited by the volatility and adsorbing propensity of the molecules involved. In any case, the odoriferous materials are not converted to less offensive compounds.

Perfume masking techniques (fragranced sprays, incenses, etc.) also leave the offending substances unchanged, which is less desirable than destroying, altering or deactivating the malodorous compounds. However, other approaches utilize chemical conversion to render malodorants innocuous. Examples of chemical conversion techniques include the use of promoters such as water-soluble ethylene oxide or propylene oxide derivatives, or mixtures of thereof. Other examples include molecules with one or more functional groups acting as a Lewis acid, Lewis base, oxidizing agent, reducing agent, or other functional group that will chemically neutralize the malodorant particles.

Finally, other techniques utilize materials that remove the malodorants from the gas phase and therefore reduce their partial pressure in the ambient air. For example, triethylene glycol, film forming polymers and cyclodextrins have been used to reduce the partial pressure of malodorants by physically removing malodor molecules from the ambient air without chemically neutralizing or altering them. In the case of triethylene glycol, the malodor molecules are partitioned into globules or droplets; in the case of film forming polymers, the malodors are "blanketed" or trapped; in the case of cyclodextrins, the malodors are trapped in the cage-like structure of cyclodextrins. In these scenarios, the malodors molecules are displaced rather than being chemically transformed into one or more less malodorous substances.

Hydrogen peroxide, an inexpensive and somewhat reactive oxidant, can also be used for malodor elimination or reduction by oxidizing malodorant molecules. However, current uses of hydrogen peroxide are limited to the use of aqueous solutions. For example, aqueous hydrogen peroxide solutions are used to remove food and smoke odors from the restaurant broiling grill emissions, in part through scrubbing of the grill exhaust gas stream through an aqueous peroxide solution. To be effective, the food must be cooked over thin, high temperature ceramic briquettes to enhance incineration of potential malodors, as well as scrubbing the grill gas stream with an aqueous hydrogen peroxide solution, followed by mixing the treated gas with ambient air prior to discharge to the atmosphere. Obviously, these systems are complex and costly and are not suitable for use by general consumers desiring to treat the air in an enclosed space.

Malodorous air may also be washed with an aqueous solution containing both hydrogen peroxide and ozone. For example, deodorization processes are known which generate and discharge ozone in combination with an atomized hydrogen peroxide solution. A reaction between ozone and atomized hydrogen peroxide generates a hydroxyl radical which is said to decompose various malodorous substances present in an indoor environment. However, the ozone generating requirement of these apparatuses makes them costly and potentially hazardous.

In a sewage treatment process, odor abatement is achieved by contacting hydrophobic components of an odor-containing gas plume condensate with odor-trapping core particles containing precipitates resulting from reaction ferrous ion, tannic acid, and hydrogen peroxide. Other processes utilize aqueous deodorant compositions containing hydrogen peroxide and nitrate ion or hydrogen peroxide, nitrate ion, and a transition metal salt. The aqueous deodorant compositions are typically mixed directly with the waste stream. Sulfide odors can be reduced or eliminated from the vapor spaces of waste handling and treatment systems by injecting a fine spray, mist or fog of an aqueous alkaline hydrogen peroxide solution into air spaces within sewage-containing system handling or treatment equipment.

Aqueous alkaline phosphate-containing hydrogen peroxide compositions for various odor elimination and disinfection uses are also known. The aqueous compositions are introduced onto surfaces and into air handling ducts by the application of a spray or mist of the aqueous alkaline peroxide solutions. The alkaline phosphate salts are said to enhance the oxidizing power of the peroxide and also to function as a peroxide stabilizer.

One catalytic process for removal of malodors from industrial gas streams includes scrubbing the gas stream through a fixed bed scrubber fitted with a solid packing bed containing a transition metal catalyst and hydrogen peroxide-containing liquor. While this technique is suitable for industrial systems, it is not applicable to home or office use.

Therefore, a need exists for malodor treatment compositions and methods which are straightforward and inexpensive to manufacture and which provide effective reduction or elimination of malodors in indoor air spaces and that can be safely used by the consuming public.

SUMMARY OF THE DISCLOSURE

In satisfaction of the aforenoted needs, an improved airborne odor elimination reduction method is disclosed that includes entraining vapor phase hydrogen peroxide (VPHP) in malodorous air and engaging the VPHP-containing malodorous air with a media comprising at least one transition metal element or compound. The media may be provided in a variety of forms, such as, but not limited to powdered materials, granular materials, filter-type structures, pad-type structures, meshes, screens, grids or any solid form capable of being supported for engaging malodorous air. The media may be porous, non-porous, permeable, or non-permeable structures, depending upon the particular product or application. The media structure may be made in whole or in part from the transition metal element or compound (e.g., powders, granular materials, solid structures comprising the transition metal element or compound); the media structure may be at least partially coated with the transition metal element or compound (e.g., filters, meshes, plates, grids, etc.). The term "media" as used herein refers to a solid structure used to provide a contact interface for the transition metal element or compound, VPHP and malodorous materials in the air.

In a refinement, the media may be a media capable of being coated, such as a woven or nonwoven filter element. The VPHP-containing malodorous air does not have to pass through the media but merely needs to engage the media so that the transition metal element or compound can catalyze the reaction between the malodorous compound and the VPHP.

Sources of the VPHP include aqueous and solid compositions disclosed in commonly assigned U.S. Patent Application Publication No. 2006/0280665, which is incorporated herein by reference. Preferably, the compositions are pH neutral to mildly acidic compositions and deliver VPHP to surrounding air by passive evaporation from a liquid or sublimation from a solid. The term passive evaporation refers to a process by which hydrogen peroxide is slowly released into the vapor phase by evaporation directly from a bulk liquid composition. This excludes processes whereby the liquid compositions are physically dispersed into the air as bulk liquid or droplets using mechanical means such as spraying, atomizing, fogging, or misting via manually operated or powered devices. The transmission of molecular hydrogen peroxide from a solid peroxohydrate compound directly to the vapor state will be described herein as a sublimation process. Preferably, the VPHP source is a solid composition as outlined in US2006/0280665, but embodiments with a liquid source of VPHP are envisioned.

In an enclosed space, the VPHP and malodorous compounds can engage the media with sufficient regularity without the need for a blower, fan or air movement mechanism. Such passive embodiments provide excellent malodor treatment in enclosed spaces of various sizes. In an active embodiment, the VPHP is entrained in a stream of the malodorous air simply by exposing at least one of the VPHP-emitting compositions to the malodorous air. Various types of fans and blowers may be utilized as described below.

In one refinement, VPHP is provided by a peroxohydrate compound selected from the group consisting of urea peroxohydrate, sodium sulfate peroxohydrate, a peroxohydrate of poly(vinylpyrrolidone) polymer and mixtures thereof. A refinement of the current invention employs a device wherein the peroxohydrate compound is provided as a powder, granule, compressed tablet or solid other form, and packaged in an air-permeable container which permits the transmission of VPHP. Malodorous air comes into contact with the device, combining with VPHP, followed by engaging the combination of the malodorous air and VPHP with the media that comprises at least one transition metal element or compound.

The media used is preferably a porous and/or permeable filter-type media coated with at least one transition metal element or compound. The VPHP-containing malodorous air flows across and/or through the media so as to engage the transition metal element or compound. The transition metal compound may be titanium dioxide ($TiO_2$) or hydrates thereof. Certain transition metal compounds, most notably certain forms of titanium dioxide, have been employed in methods that eliminate malodors through a photocatalytic process using ultraviolet (UV) light. While the disclosed methods employ transition metal compounds to chemically transform/destroy malodors, no UV or other light source is required. The inventors have surprisingly found that the transition metal compound(s) satisfactorily catalyze the chemical transformation/destruction of the malodors by the VPHP entrained in the malodorous air in the absence of UV light, thereby safely and effectively reducing or eliminated the malodors, without resorting to the potentially hazardous use of UV light. Further, the working elements of the disclosed apparatus may be housed in an opaque housing, non-transparent to UV or visible light, having a wavelength from about 200 to about 800 nm. While certain transition metal compounds or hydrogen peroxide alone may individually have the ability to eliminate malodors, the disclosed combination of using at least one transition metal element or compound with VPHP is positively synergistic, providing faster and more effective malodor elimination.

In a refinement, one disclosed method for reducing malodors from an air stream, comprises; providing vapor phase hydrogen peroxide across and/or through a media that is disposed in an area with malodorous compounds in the ambient air, wherein at least a portion of the exterior surface of the media comprises at least one transition metal element or compound.

In a refinement, the transition metal(s) are selected from the group consisting of titanium, vanadium, manganese, iron, cobalt, molybdenum, tungsten, nickel, silver, copper and zinc. Preferably, the transition metal(s) are selected from the group consisting of titanium, vanadium, manganese, iron, copper, molybdenum, tungsten and zinc for reasons of low-cost, low toxicity and minimal environmental impact.

In another refinement, the transition metal compounds(s) are selected from the group consisting of one or more titanium-containing compounds.

In another refinement, the transition metal compound is selected from the group consisting of titanium dioxide hydrates, and mixtures thereof.

In another refinement, the transition metal compound-containing coating on the media also contains one or more catalyst promoter compounds that comprise a salt comprising a non-transition metal cation and an anion selected from the group consisting oxide, hydroxide, halide, carbonate, borate, phosphate, sulfate, nitrate, silicate, aluminate, borate aluminate, carboxylate, stannate, and bismuthate.

In another refinement, the vapor phase hydrogen peroxide is provided through passive evaporation of a pH neutral to mildly acidic liquid aqueous composition containing hydrogen peroxide.

In another refinement, the vapor phase hydrogen peroxide is provided through sublimation of hydrogen peroxide from a solid composition containing a hydrogen peroxide complex. In another refinement, the vapor phase hydrogen peroxide is provided by sublimation of hydrogen peroxide from a solid composition including at least one pH neutral to slightly acidic peroxyhydrate compound. In still another refinement, the solid composition comprises from about 0.1 wt % to about 50 wt % hydrogen peroxide. Preferably, the solid composition is a powder, granule, compressed tablet or crystalline solid form. Further, the solid composition is preferably contained within a porous (gas permeable) container, such as a porous, replaceable pouch. Preferably, the solid composition is one of the peroxohydrate compositions set forth in US2006/0280665.

In another refinement, the solid composition further comprises one or more of the following: fragrances, colorants, surfactants, solvents, binders, processing agents and hydrogen peroxide-stabilizing agents.

In a refinement, one or more color change indicators are provided for alerting the user when the device is functional and/or activated and/or when the VPHP supply has become depleted. Specifically, in one refinement, the transition metal compound changes color in the presence of VPHP to indicate to the user that the device is functional. The user may also be alerted that VPHP is not present in sufficient amounts when a second color change occurs, thus the VPHP supply needs to be replenished. Using titanium dioxide as an example, the color change changes from white to yellow in the presence of VPHP, and will revert back to white when the supply of VPHP is exhausted.

In a refinement, a product may be provided in the form of a non-woven sachet that encloses a solid composition that releases VPHP. The presence of the VPHP causes the catalyst coating of a non-woven to undergo a distinct color change. When the color fades, the consumer will know to either replenish the VPHP source within the sachet or purchase a new product.

Various apparatuses are disclosed for treating malodors in air. One disclosed apparatus comprises a passive device whereby a media comprising a transition metal compound is placed near a VPHP source. The VPHP source may be solid material disposed within a pad or a supply of liquid material disposed adjacent to the pad. The transition metal compound may be coated onto the pad or may be media disposed within or otherwise supported by the pad. Embodiments with solid VPHP disposed within a coated filter pad are preferably disposable products while embodiments with a coated pad disposed near a liquid or solid VPHP source disposed outside of the pad may be rechargeable products.

Disposable pads with a solid source of the VPHP disposed therein may be conveniently used within or near garbage cans, litter boxes, shoes, laundry (diaper) hampers, etc.

Passive devices with a liquid source of VPHP may be provided in the form of a decorative vase with a transition metal compound media disposed above the liquid source of the VPHP. Various other decorative and functional embodiments will be apparent to those skilled in the art.

Other "active" or "mechanical" devices comprise an air movement mechanism for generating an air stream from ambient air that comprises air and malodorants. The apparatus may further comprise a vapor phase hydrogen peroxide generator and a media whose surface is coated with at least one transition metal element or compound. The vapor phase hydrogen peroxide generator is positioned "upstream" with respect to the air movement through the apparatus such that hydrogen peroxide vapor first becomes entrained in the malodorous air stream, followed by at least partial engagement/interaction with the filter media surface that is coated with at least one transition metal element or compound.

In one preferred embodiment, the air movement mechanism is a fan.

In another refinement, the VPHP source container is disposed upstream of the media, which is itself upstream from the air displacement mechanism. Thus, the air displacement mechanism draws the malodorous air stream across/through the VPHP source container, across and/or through the media and past/through the air displacement mechanism.

In another refinement, the apparatus further comprises a vented base disposed "downstream" from the air displacement mechanism and the media. Thus, the malodorous air passes across/through the VPHP source container, through/across the media, past the air displacement mechanism, and exits the apparatus via a vented base comprising a plurality of vent openings. An object which emits a fragrance may be positioned within the base.

In another refinement, the VPHP source container comprises a porous (gas permeable) pouch and the apparatus further comprises a structure which supports the porous pouch. In such a refinement, the vertical chimney may be connected to a central housing that accommodates the filter. The central housing may include vents for the axial flow of air. Further, the central housing can be connected to a vented base that accommodates and houses the air displacement mechanism and which includes at least one opening for the release of air that is passed through the vertical chimney, porous pouch, central housing and filter and past the air displacement mechanism. In another refinement, the vertical chimney is cylindrical in shape.

One preferred apparatus for treating malodors in air comprises an air movement mechanism for generating an air stream using ambient air that comprises indoor air and malodorants. The air movement mechanism is accommodated in a vented base comprising a plurality of vent openings. The vented base is connected to a central housing disposed on top of the vented base. The central housing accommodates a media comprising at least one transition metal element or compound and the central housing is disposed between the vented base and a chimney or top housing. The chimney accommodates a porous pouch containing solid peroxohydrate compound that serves as a VPHP generator/source. The central housing and chimney are vented so as to permit an axial airflow across and/or through the porous pouch, across/through the media, and to the air movement mechanism. The air movement mechanism accordingly draws the air stream and malodorants downward through the chimney and across and/or through the porous pouch where vapor phase hydrogen peroxide (VPHP) is entrained in the air stream before the malodorous air stream and VPHP pass across and/or through and a least partially engage the media where at least a portion of the malodorants react with VPHP on the media. Finally, the air stream, partially/fully depleted of malodorants, passes out of the apparatus through the openings in the vented base.

Other advantages and features will be apparent from the following detailed description when read in conjunction with the attached drawings.

BRIEF DESCRIPTION OF THE DRAWINGS

For a more complete understanding of the disclosed methods and apparatuses, reference should be made to the embodiment illustrated in greater detail on the accompanying drawings, wherein.

It should be understood that the drawings are not necessarily to scale and that the disclosed embodiments are sometimes illustrated diagrammatically in partial views. In certain instances, details which are not necessary for an understanding of the disclosed methods and apparatuses or which render other details difficult to perceive may have been omitted. It should be understood, of course, that this disclosure is not limited to the particular embodiments illustrated herein

DETAILED DESCRIPTION

Hydrogen peroxide in its pure form is a clear, colorless liquid having a slightly sharp acrid odor and a freezing point of −0.4° C. Pure liquid hydrogen peroxide exhibits a vapor pressure of about 2 mmHg at 25° C., somewhat less than that of water (~24 mmHg at 25° C.). Aqueous solutions of hydrogen peroxide exhibit a mixed vapor phase composition of water vapor and vapor phase hydrogen peroxide, as expected for a mixture of two miscible volatile liquids. See, for example, *Hydrogen Peroxide*, Kirk-Othmer Encyclopedia Chemical Technology, 4$^{th}$ Edition, Volume 13, 1995, Wiley-Interscience Publication, and references therein.

Inorganic and organic compounds containing molecular hydrogen peroxide as solid/crystalline adducts are referred to as peroxohydrates or perhydrates. Many such materials are known in the commercial and technical literature, including such materials as sodium carbonate peroxohydrate $2Na_2CO_3.3H_2O_2$ (sodium percarbonate); ammonium carbonate peroxohydrate $(NH_4)CO_3.3H_2O_2$; urea peroxohydrate, $CO(NH_2)_2.H_2O_2$ (urea peroxide); sodium sulfate peroxohydrate, $2Na_2SO_4.H_2O_2.H_2O_2$; and various peroxohydrate phosphate salts. Descriptions of various peroxohydrates can be found in "Hydrogen Peroxide, Peroxohydrates", Kirk-Othmer Encyclopedia of Chemical Technology, 4$^{th}$ Edition, Volume 13, 1995, Wiley-Interscience Publication, and therein. A polymer-containing peroxohydrate of poly(vinyl pyrrolidone), $PVP.H_2O_2$, where the hydrogen peroxide content of the compound is variable up to about 22 wt % of the composition, is commercially available as Peroxydone® from the ISP Corporation, Wayne, N.J., USA.

Aqueous liquid compositions containing hydrogen peroxide, wherein the pH of the solution is about 8 or below, can be passively evaporated in an indoor environment to produce useful amounts of vapor phase hydrogen peroxide with utility toward the elimination or reduction of malodors from the air space and surfaces of the indoor environment. Alkaline aqueous hydrogen peroxide solutions are not stable. Therefore, it is desirable to utilize pH neutral to mildly acidic aqueous hydrogen peroxide compositions in the pH range of about 1 to about 8. This provides acceptable long-term stability of the aqueous hydrogen peroxide composition. More preferably, the pH of the liquid composition is in the range of about 2 to about 7. Most preferably, the pH of the liquid composition is in the range of about 3 to about 6, provided for optimal product stability.

The aqueous pH neutral to mildly acidic aqueous hydrogen peroxide compositions may be homogenous solutions or heterogeneous dispersions containing suspended solids. The viscosity of the liquid hydrogen peroxide compositions may range from that of a "water-thin" fluid (less than about 10 cp at 25° C.) to that of a highly viscous, rigid gel, paste or suspension (about 100,000 cp or greater at 25° C.). Viscosity building agents may include peroxide-stable surfactant systems, peroxide-stable polymers, as well as various solid inorganic thickening agents/fillers such as alumina, silica, and natural/synthetic clays.

The concentration of hydrogen peroxide in the aqueous compositions may comprise up to about 50 wt % of the composition, preferably less than about 10 wt % of the composition and most preferably from about 0.5% to 8 wt % of the composition. The aqueous compositions may include minor amounts of the other ingredients, including fragrance ingredient and fragrance solubilizing agents such as surfactants or solvents, and/or colorant(s) for aesthetic purposes. For optimal stability, the aqueous compositions may also include one or more hydrogen peroxide-stabilizing agents, such as, for example, stannate compounds, phosphate salts, organophosphonates, and various chelating agents derived from aminocarboxylates or aminophosphonates. Various peroxide-stabilizing agents are disclosed in "Hydrogen Peroxide, Stabilization", Kirk-Othmer Encyclopedia of Chemical Technology, $4^{th}$ Edition, Volume 13, 1995, Wiley-Interscience Publication and the referenced therein, incorporated herein by reference. Additional ingredients may include peroxide-stable acids for pH adjustment, including but not limited, to sulfuric acid, adipic acid, glutaric acid, succinic acid, and polyacrylic acid.

Various dispensing devices are suitable for malodor reduction or elimination applications using passive generation of vapor phase hydrogen peroxide from the low viscosity aqueous hydrogen peroxide-containing solutions. Liquid wicking devices, such as container-dispensing systems for liquid air fresheners, are especially useful as they may be exposed to an induced air stream within a housing relatively easily. Materials of construction for such devices are selected so as to provide for the integrity of the container-dispenser with respect to the oxidizing and corrosive nature of the aqueous hydrogen peroxide solutions described herein.

Viscous gels or suspensions may be contained within dish, or cup-type containers accommodated within a housing and having at least one opening so as to permit the passive evaporation of the hydrogen peroxide and entrainment of the generated VPHP into the induced air stream, producing a suitable concentration of vapor phase hydrogen peroxide in the air stream before it engages the media.

Various mechanical devices may be utilized in combination with hydrogen peroxide-containing viscous gels or suspensions of the present invention. These devices include those which will enhance effective generation of vapor phase hydrogen peroxide within the indoor environments by utilizing mild heating of the compositions, which are enclosed within appropriate containers, pouches or packages. Such heating devices, used to promote the dispensing of volatile liquid compositions, include those disclosed in U.S. Pat. Nos. 3,633,881; 4,020,321; 4,969,487; 5,038,394; 5,290,546; 5,647,053; 5,903,710; 5,945,094; 5,976,503; 6,123,935; and 6,862,403 B2, incorporated herein by reference. Fan type devices are employed to generate an air stream with entrained VPHP which is then flowed across and/or through the media. Such fan type devices include those disclosed in U.S. Pat. Nos. 4,840,770; 5,370,829; 5,547,616; 6,361,752 B1 and 6,371,450 B1, incorporated herein by reference.

Certain solid peroxohydrate compounds, when exposed to ambient indoor air, will surprisingly liberate useful amounts of vapor phase hydrogen peroxide with utility towards reduction or elimination of malodors from the air space and surfaces of the indoor environment. These peroxohydrate compounds may comprise part, or all, of solid compositions which sublime hydrogen peroxide from the solid composition into the vapor phase at ambient room temperatures. The amount of peroxohydrate utilized in the solid composition will depend on the hydrogen peroxide content of the peroxohydrate and the release rate of hydrogen peroxide vapor from a given peroxohydrate, relative to the desired rate of release for the composition containing the peroxohydrate. Ambient indoor air generally contains a significant amount of water vapor, and alkaline peroxohydrate compounds are unstable in the presence of moisture. Thus, it is necessary to utilize pH neutral to slightly acidic peroxohydrate compounds. The terms "pH neutral to slightly acidic peroxohydrate compound' refers to a peroxohydrate compound wherein the pH of a concentrated (~5 wt % in water) solution of the compound in purified water is less than about a pH of about 9 when the solution is at a temperature range of from about 20 to about 25° C.

Examples of suitable mildly acidic hydrogen peroxide-containing solid peroxohydrate compounds include urea peroxohydrate, $CO(NH_2)2.H_2O_2$; sodium sulfate peroxohydrate, $2Na_2SO_4.H_2.2OH_2.H_2$, and a peroxohydrate of poly (vinyl pyrrolidone) polymer, $PVP.H_2O_2$, where the hydrogen peroxide content of the polymeric PVP peroxohydrate can range up to about 22 wt %. The solid composition containing one or more peroxide-containing peroxohydrate compounds may also include one or more non-peroxide containing filler solids, such as inert inorganic salts, alkaline earth sulfate salts, silica, alumina and talc.

The solid composition may comprise a powder, compressed tablet, crystalline, solid, or other readily recognizable solid forms. The hydrogen peroxide content of the solid composition can be as high as about 50 wt % hydrogen peroxide, but preferably about 25 wt % or less for reasons of, among other things, product processing and stability. More preferably, the solid compositions may have hydrogen peroxide content in the range of from about 5 to about 25 wt %. Most preferably, the solid compositions may have a hydrogen peroxide content in the range of from about 10 to about 22 wt %.

The solid composition may include minor amounts of other ingredients, including fragrance ingredients, and/or colorant (s) for aesthetic purposes. Minor amounts of other ingredients, such as surfactants, solvents, and processing aids (e.g., anti-caking, mold release agents, shape-forming agents or binders, etc.) may also be included in the solid compositions. For optimal peroxide stability, the compositions may also include one or more hydrogen peroxide-stabilizing agents, such as stannate compounds, phosphate salts, organophosphonates, and various chelating agents derived from aminocarboxylates or aminophosphonates. Various peroxide-stabilizing agents are disclosed in "Hydrogen Peroxide, Stabilization", Kirk-Othmer Encyclopedia of Chemical Technology, $4^{th}$ Edition, Volume 13, 1995, Wiley-Interscience Publication and references therein, incorporated herein by reference.

The solid hydrogen peroxide-containing VPHP-generating compositions may be packaged within various types of porous containers which permit the transmission of vapor phase hydrogen peroxide into the indoor air space and permit the flow of an air stream across and/or through the container. These packages include pouches or bags, which allow for the transmission of hydrogen peroxide vapor and an induced air stream through the package walls. The solid compositions may also be contained within a cup or dish having one or more suitable openings which permit vapor phase hydrogen peroxide transmission from within the container into the indoor air space. If the solid hydrogen-peroxide-containing compositions are of a powdered, granule, or particulate form, a container such as a dish or cup may include a physical barrier preventing the solid from being discharged from the container by shaking, inverting, or the like. Appropriate physical barriers include a covering of fabric or screen-type material of sufficiently small pore/mesh size, such that the solid powder or particulate cannot pass through the fabric/screen, however the pores in the covering will allow for the transmission of vapor phase hydrogen peroxide into said air stream and downstream towards the disclosed media disposed within the apparatus.

Figure 1:
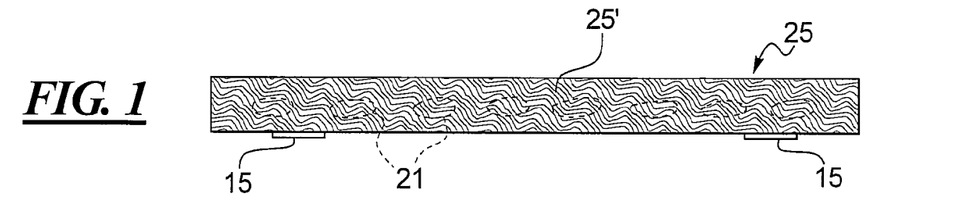
FIG. 1 is a side view of a media comprising a transition metal element or compound made in accordance with the present disclosure with a solid source of VPHP disposed within the media that can be used in both passive (FIGS. 2-6) as well as active (FIGS. 7-17) malodorants treatment systems.
Figures 2, 3, 4, 5, 6:
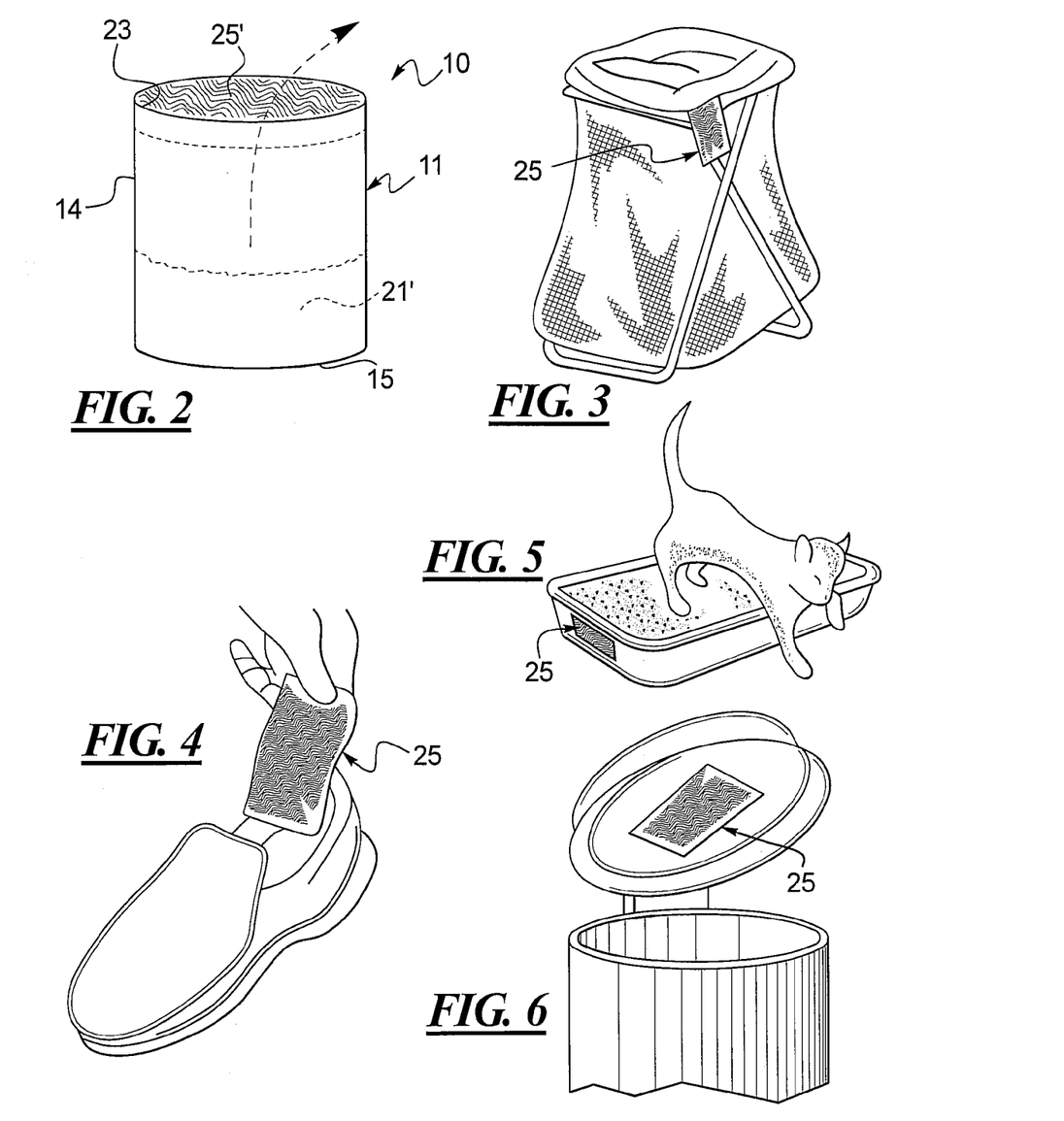
FIG. 2 is a perspective view of a passive malodor treatment apparatus that includes a liquid source of VPHP disposed below a media.
FIG. 3 is an illustration of the use of the pad-type media of FIG. 1 on a laundry (diaper) hamper.
FIG. 4 is an illustration of the use of the pad-type media of FIG. 1 in a shoe.
FIG. 5 is an illustration of the use of the pad-type media of FIG. 1 on a litter box.
FIG. 6 is an illustration of the pad-type media of FIG. 1 on the underside of a lid of a kitchen garbage can.
Figure 7:
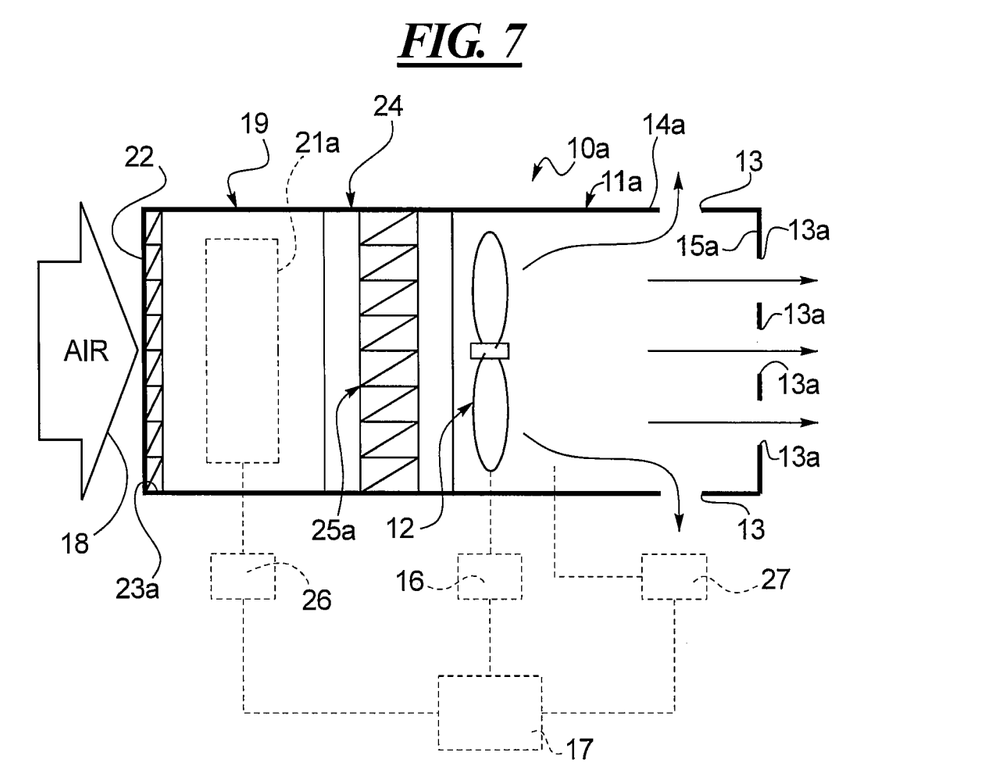
FIG. 7 is a schematic diagram of a disclosed apparatus for catalytically treating airborne malodorants with vapor phase hydrogen peroxide; and at least one transition metal element or compound.

Preferred sources of hydrogen peroxide are provided in a powder form disposed within a pouch. Preferably, the hydrogen peroxide source is a peroxohydrate compound derived from hydrogen peroxide and polyvinyl pyrrolidone, sold as Peroxydone® by ISP Corporation, Wayne, N.J., USA. The $PVP.H_2O_2$ may be provided in a Tyvek® pouch, also sold by DuPont of Wilmington, Del., USA. The pouch may be provided in a variety of shapes and sizes including but not limited to the annular-shaped pouch 121 shown in FIG. 10.

The inventive apparatus serves to reduce/eliminate malodorous substances from an indoor air stream, by passing said air stream through a device which mixes VPHP with the air stream, followed by interaction of said air stream with a media comprising or coated with at least one transition metal element or compound.

Preferred transition metal(s) may be selected from the group consisting of titanium, vanadium, manganese, iron, cobalt, molybdenum, tungsten, nickel, silver, copper and zinc. Most preferred transition metal(s) are selected from the group consisting of titanium, vanadium, manganese, iron, copper, molybdenum, tungsten, and zinc for reasons of low-cost, low toxicity and minimal environmental impact. Various titanium-containing compounds are especially desirable. Among these, transition metal compounds selected from the group consisting of titanium dioxide and titanium dioxide hydrates, and mixtures thereof are most desirable in terms of cost and low environmental impact.

One or more catalyst promoter compounds may be used such as non-transition metal oxides, hydroxides, carbonates, borates, phosphates, halides, silicates, aluminates, nitrates, sulfates, organo-carboxylates, stannates, and bismuthates. Illustrative examples include (without limitation): alkali metal and alkaline earth halides, alkaline earth oxides/hydroxides, alkali metal and alkaline earth carbonates, alkali metal and alkaline earth sulfates, alkali metal and alkaline earth silicates, silica, alkali metal and alkaline earth aluminates, alumina, alkali metal and alkaline earth borates, boric acid, alkali metal and alkaline earth phosphates, Sn oxide/hydroxide compounds, and Bi oxide/hydroxide compounds.

The disclosed device disclosed herein employs a media, the surface of which comprises or is at least partially covered/coated with at least one transition metal element or compound. The media may be fibrous or non-fibrous in nature. The media may be permanent within the device (i.e., not intended for replacement over the useful lifetime of the device) or it may be replaceable (i.e., periodic replacement of "spent" filters, with installation of new/fresh media). The media may be made from a variety of materials including woven fabric, non-woven fabrics, glass wools, or sintered glass beads. The media comprises or is at least partially coated with a composition containing at least one transition metal element or compound. The loading of said transition metal coating on or into the media will range from about 0.001 wt % to about 50 wt %. Examples of preferred media include synthetic woven fabrics, synthetic non-woven fabrics, and glass wools. Highly preferred media include synthetic non-woven fabrics. Representative examples of various synthetic non-woven fabrics (fiber compositions and manufacturing processes) can be found in "Non-woven Fabrics", Kirk-Othmer Encyclopedia of Chemical Technology, $4^{th}$ Edition, John Wiley & Sons, Inc., copyright© 1996, incorporated herein as a reference. Non-woven fabrics composed of synthetic fiber materials which are resistant to the oxidizing action of hydrogen peroxide are especially preferred. Such oxidation-resistant materials include polyolefin (especially polyethylene and polypropylene) and polyester fibers.

Examples of preferred media include synthetic non-woven fabrics comprised of polyester and/or polyolefin fibers, wherein said fibers are at least partially covered or coated with at least one transition metal element or compound. Highly preferred coatings contain titanium dioxide. In this embodiment, the media is coated with a material comprising from about 0.001 to about 50 wt % (combined) of titanium dioxide and/or hydrated titanium dioxide. Said transition metal element(s) and compound(s) may be adhered or bonded to the surface of the media through the use of various inorganic or organic adhesion agents. Preferably such adhesion agents are resistant to oxidation by hydrogen peroxide.

In a preferred representative embodiment, the filter comprises from about 90 to about 99.99 wt % non-woven air-spun polyester fibers, and from about 0.01 to about 10 wt % of a powdered coating that comprises a mixture of titanium dioxide and hydrated titanium dioxide.

Low concentrations of vapor phase hydrogen peroxide contained within an malodorous indoor air environment, generated using methods employing passive evaporation of pH neutral to mildly acidic aqueous liquid compositions containing hydrogen peroxide, or sublimation of hydrogen peroxide vapor from solid compositions containing at least one pH neutral to mildly acidic solid hydrogen peroxide-containing peroxohydrate compound, where said VPHP and malodor interacts with at least one transition metal element or compound, have excellent utility towards reduction or elimination of malodors from the air space and surfaces of the indoor environment. In particular, such VPHP sources combined with at least one transition metal element/compound acting as a catalyst are useful for the reduction or elimination of tobacco smoke odors and various other malodors, especially those containing reduced sulfur and nitrogen compounds, from the air space within indoor environments.

Passive odor removing systems are illustrated in FIGS. 1-6. In FIG. 1, a non-woven media or pad 25 is shown with solid VPHP sources 21 that can be in powdered, tablet or granular form. The non-woven fibers 25' are coated with a catalyst material, such as a transition metal compound, such as titanium dioxide. The pad 25 may include one or more adhesive strips 15 for adhering the pad 25 in place such as to a laundry hamper (FIG. 3), in a shoe (FIG. 4), to a litter box (FIG. 5) or to a garbage can (FIG. 6).

FIG. 2 illustrates a different type of passive device that includes a container 11 with a cylindrical sidewall 14 and bottom 15. A liquid source of VPHP 21' is provided inside the container 11 and a coated pad 25' (without a solid source of VPHP disposed therein) is accommodated in the opening 23 of the container 11. Ambient air, containing malodors engages the pad 25' and comes into contact with the VPHP exiting the container 11 through the pad 25'.

In contrast to the passive devices of FIGS. 2-6, active apparatuses 10*a*, 100 are illustrated in FIGS. 7 and 8-17. Turning to FIG. 7, the apparatus 10*a* includes a base housing 11*a* which accommodates a fan 12 and which provides openings or vents 13 in the sidewall 14*a* or, in the alternative, vents 13*a* disposed in the end or bottom wall 15*a*. The base 11*a* both houses and supports the fan 12, which is illustrated in greater detail in connection with the embodiment 100 of FIGS. 14 and 15. Still referring to FIG. 7, the fan 12 is powered by a motor 16 which, in turn, is linked to a control module or user interface 17. The fan 12 creates an air stream flowing in the direction of the arrow 18 towards and through the upper or chimney section 19. The chimney section 19 accommodates a vapor phase hydrogen peroxide (VPHP) generator 21*a* which, in one refinement, comprises a pouch containing several grams of a powdered peroxohydrate compound such as Peroxydone®. A dust collector or preliminary filter 22 covers the open end 23 of the chimney or housing 19.

The chimney 19, with the VPHP generator 21a is connected to a middle housing 24 which accommodates the primary filter 25a. The filter 25a preferably comprises a nonwoven polyester coated with one or more transition metal compounds such as titanium dioxide and aluminum dioxide. It has been found that the combination of VPHP and a transitional metal compound such as titanium dioxide provide a synergistic effect with respect to oxidizing airborne malodorous materials, thereby resulting in the accelerated reduction/elimination of the malodor material from an indoor airspace. The apparatus 10 provides an excellent mechanism for exploiting this synergy.

The release of VPHP may be enhanced by employing a heater 26 which would also be linked to the interface of 17. Further, additives may be included in the VPHP generator 21a as discussed above or additional materials may be entrained in the air stream by either injection or evaporation. Therefore, additional materials may be provided by one or more supply chambers shown schematically at 27. The supply chamber 27 may also be equipped with a heating device which would be linked to the interface 17.

Figure 8:
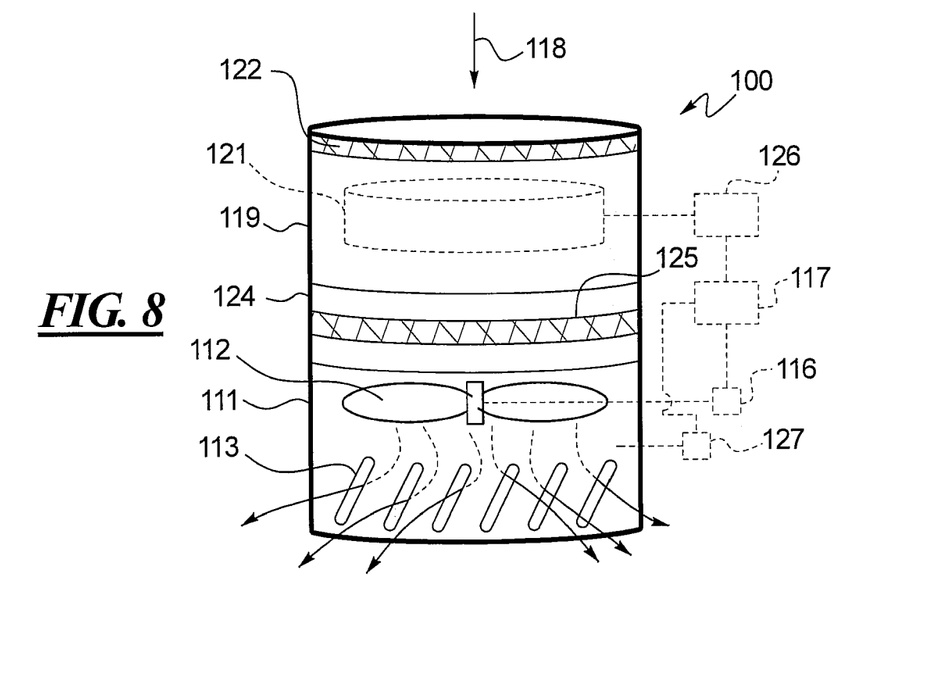
FIG. 8 is a schematic/front plan view of a disclosed apparatus for catalytically treating airborne malodorants with vapor phase hydrogen peroxide; and at least one transition metal element or compound.

Turning to FIG. 8, an apparatus 100 is shown in a more preferred upright configuration. The apparatus 100 includes a chimney or top section 119, a middle housing section 124 and vented base 111. The fan 112 draws air downward in the direction of the arrow 118 through the VPHP generator 121 where hydrogen peroxide vapor is entrained in the air stream before the air stream passes across and/or through the coated filter 125. Malodorants contained within the air stream may then by catalytically oxidized by the hydrogen peroxide vapor in combination with the transition metal element/compound that coats the filter 125. The "cleaned" air is then distributed out through the vents 113 as shown. An optional heater is shown at 126 which is linked to the interface 117 which, in turn, is also linked to the fan motor 116 and an optional active dispenser/heater 127. The optional dust filter/collector is shown at 122.

Figure 9:
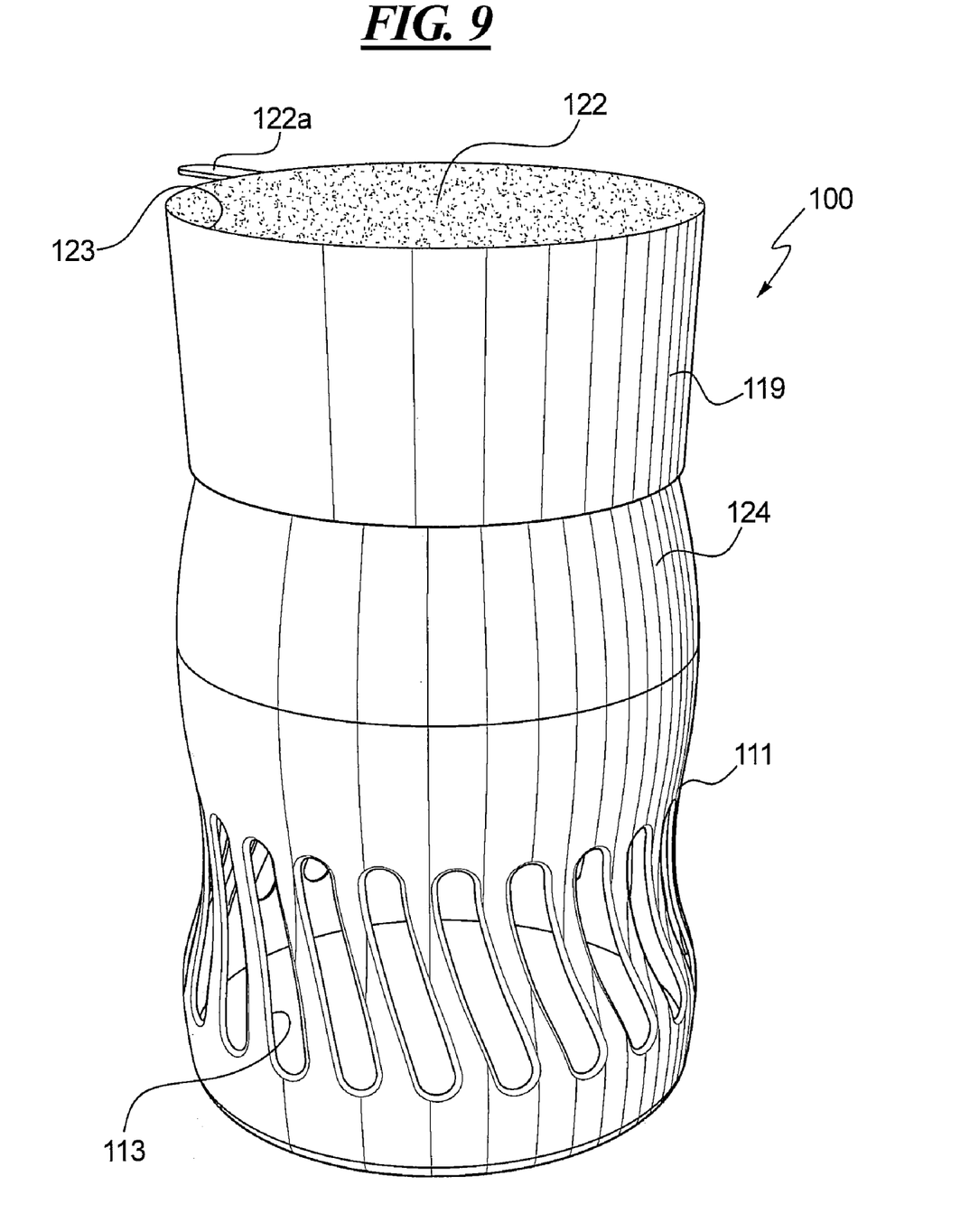
FIG. 9 is a front plan/perspective view of the apparatus shown in FIG. 8.

Turning to FIG. 9, the apparatus 100 is shown with the preferred configuration of the vents 113 in the lower base housing 111 for providing the airflow patterns described in greater detail below in connection with FIGS. 16-17. The middle housing 124, upper housing 119 and lower base housing 111 may be manufactured from the same plastic, and preferably opaque, material. The optional dust filter/collector 122 is shown with a tab 122a for facilitating insertion and removal of the filter 122 from the top opening 123 of the chimney 119.

Figure 10:
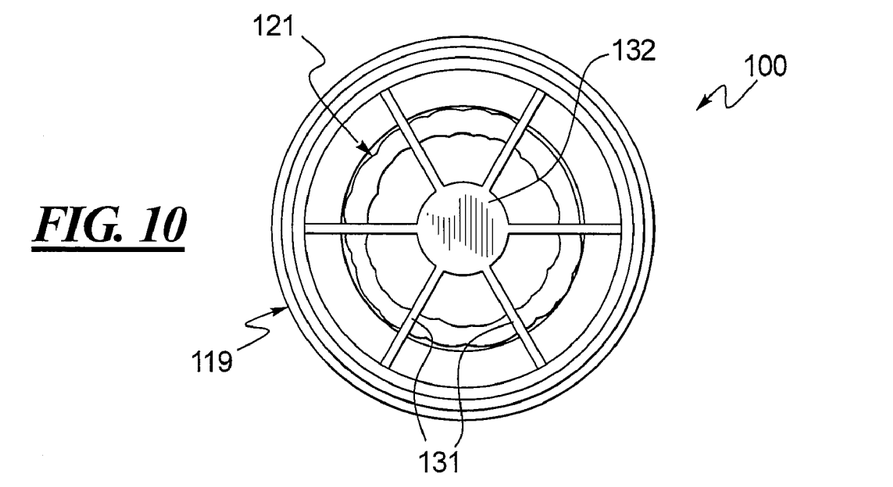
FIG. 10 is a bottom plan view of the upper housing or chimney showing an annular hydrogen peroxide emitting pouch.
Figure 11:
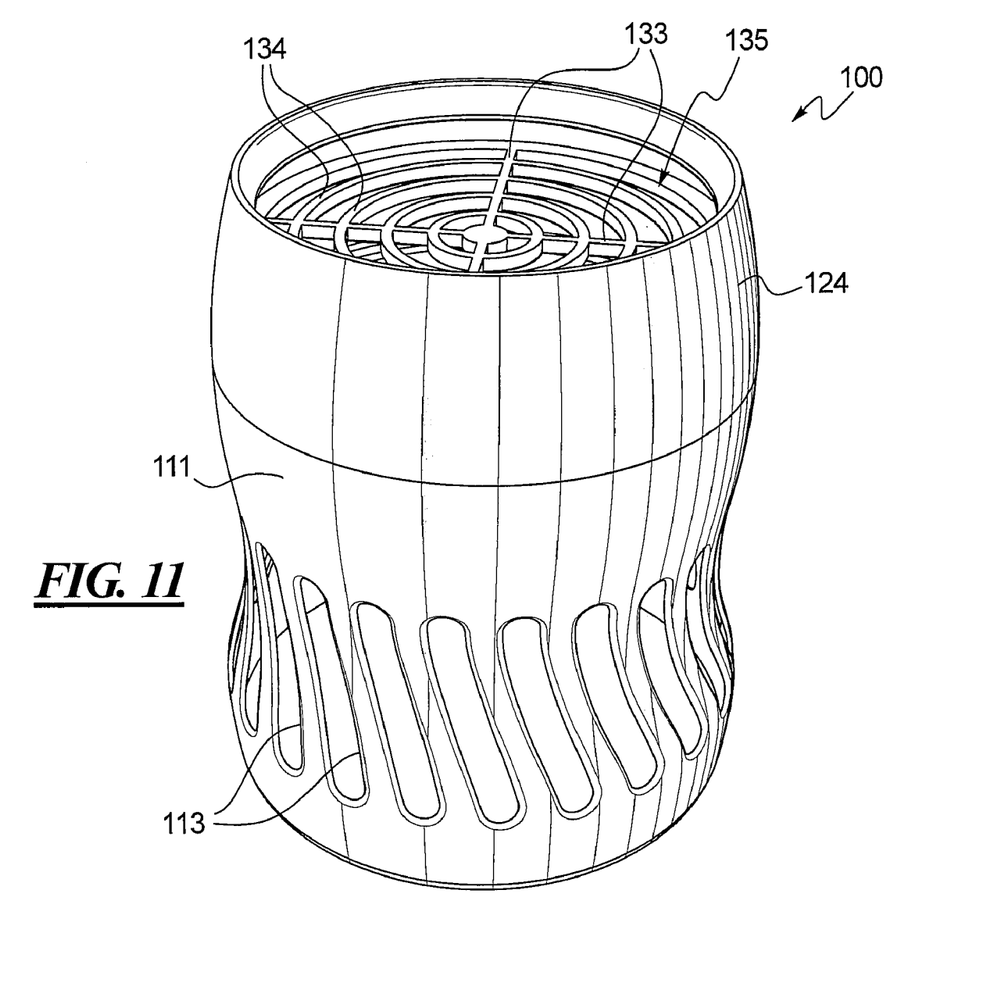
FIG. 11 is a perspective view of the lower vented base and middle housing that accommodates a media that is coated with at least one transition metal element or compound.
Figure 12:
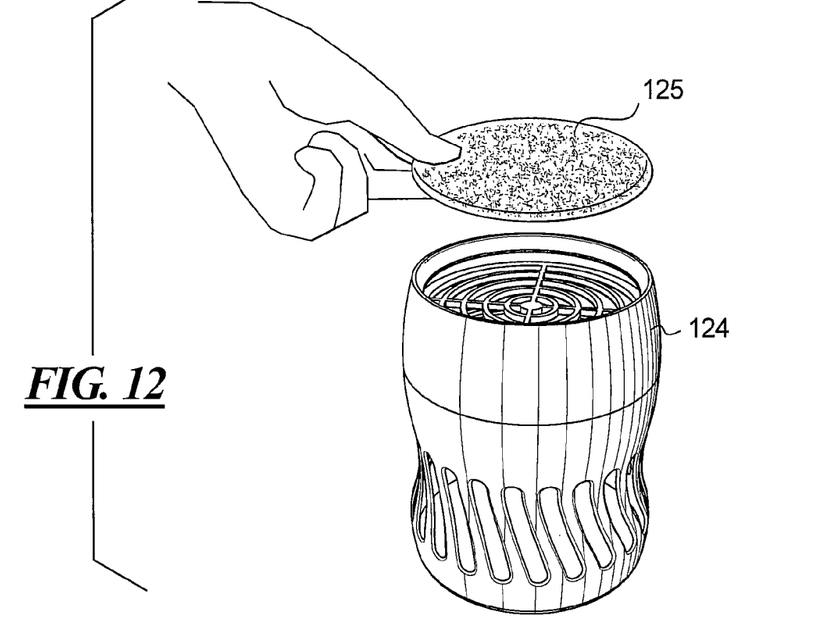
FIG. 12 is a perspective view illustrating the installation of the media comprising a transition metal elements(s)/compound(s) into the middle housing.
Figure 13:
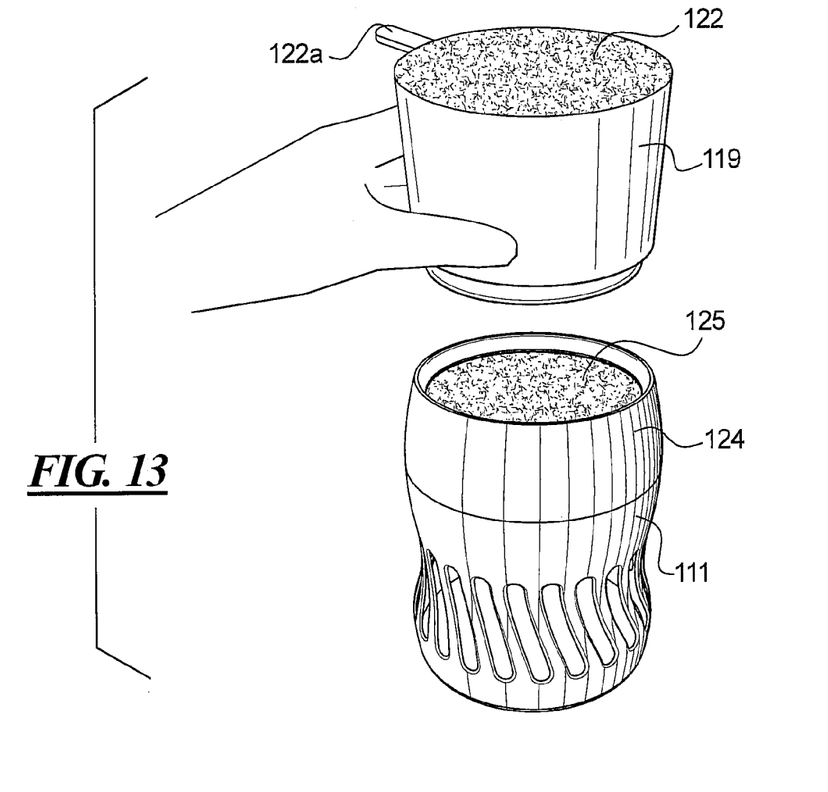
FIG. 13 is a perspective view illustrating installation of the upper housing or chimney that is equipped with the hydrogen peroxide emitting pouch onto the middle housing that accommodates the media comprising the transition metal element (s)/compounds(s)

FIG. 10 is a bottom plan view of the chimney or upper housing 119. A grate or support for the VPHP generator 121 is provided by a series of radial spokes 131 connected to a center plate 132. Turning to FIG. 13, the chimney 119 fits on top of the middle housing 124. The middle housing 124 also includes a grate 135 comprising a plurality of radial spokes 133 connected to a series of concentric rings 134. The grate 135 supports the coated filter 125 (not shown in FIG. 10; see FIG. 11). FIGS. 12 and 13 illustrate the insertion of the coated filter 125 into the middle housing 124 and the subsequent placement of the chimney 119 on top of the middle housing 124.

Figure 14:
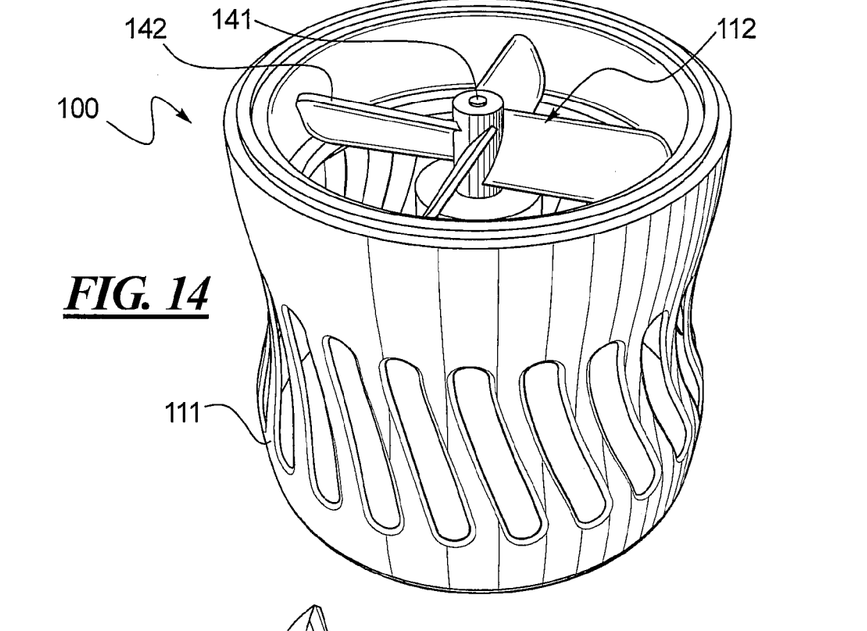
FIG. 14 is a perspective view of the vented base housing and fan of the disclosed apparatus as illustrated generally in FIG. 9 and FIGS. 11-13.
Figure 15:
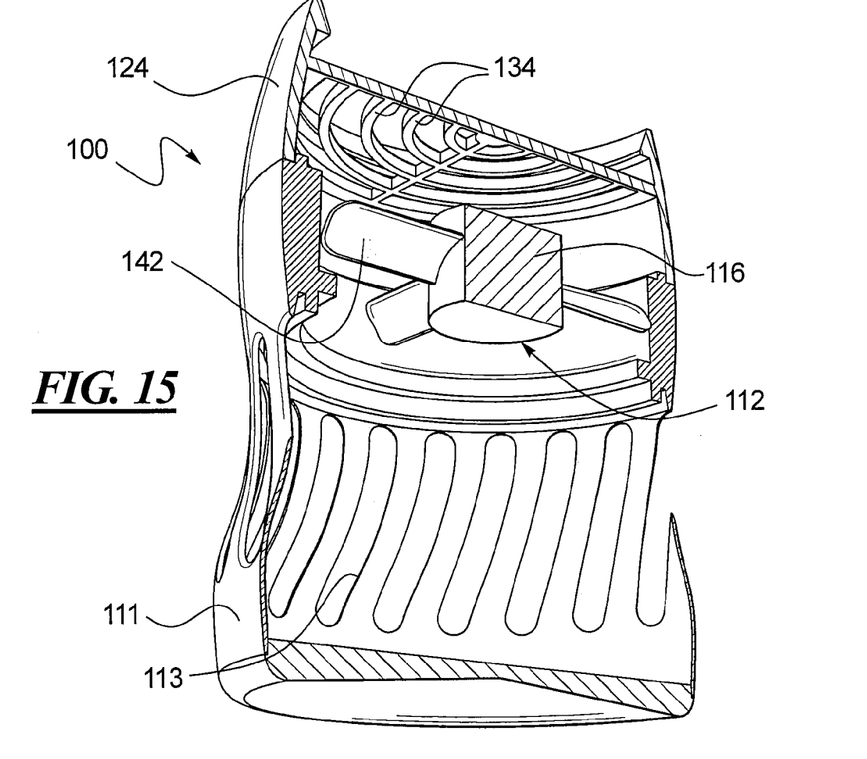
FIG. 15 is a perspective/sectional view of the vented base housing, a fan and middle housing that accommodates the media of the disclosed apparatus as shown in FIG. 12.

FIG. 14 is a perspective view of the lower base housing 111, which accommodates the fan or air movement mechanism 112. The middle housing 124 and chimney 119 are removed. The fan 112 includes a shaft 141 coupled to the motor 116 (see FIGS. 8 and 15) and a plurality of radial blades 142.

Figure 16:
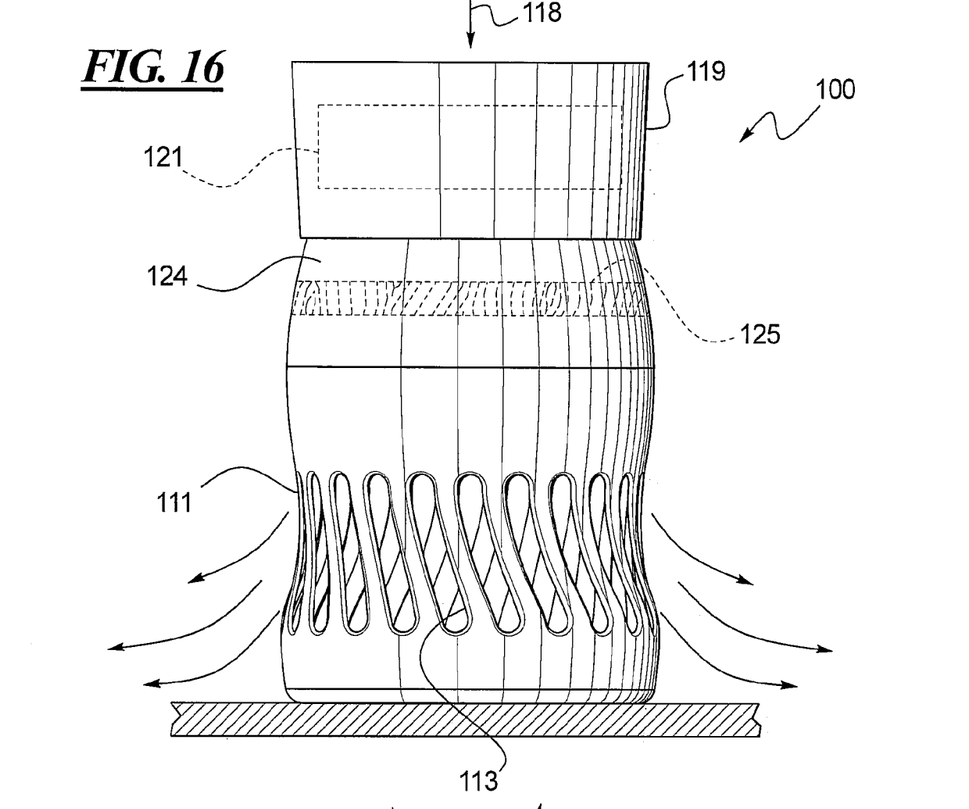
FIG. 16 is a front plan view of a disclosed apparatus generally illustrating the induced airflow stream.
Figure 17:
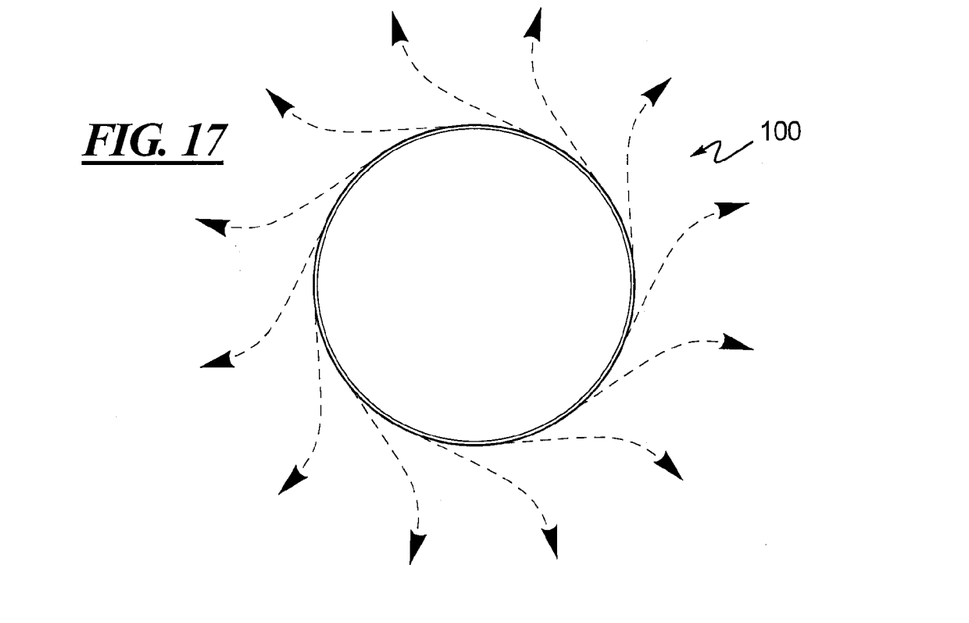
FIG. 17 is a top plan view of the apparatus as shown in FIG. 16 generally illustrating the induced airflow exiting the apparatus.

FIGS. 16-17 illustrate the airflow generated by the apparatus 100. Air is drawn downward in the direction of the air 118 by the air displacing action of the fan 112. VPHP becomes entrained in the air stream as it passes through the chimney 119 which includes the VPHP generating pouch 121. The air stream, that includes malodor-causing molecules as well as VPHP, then passes across and/or through the coated filter 125 of the middle of the housing 124. Malodor-causing molecules are then catalytically oxidized by hydrogen peroxide in the presence of the transition metal element/compound that is coated on the filter 125. The vents 113 in the base housing 111 provide the airflow pattern illustrated in FIGS. 16-17 as further explained in co-pending and commonly-assigned U.S. patent application Ser. No. 11/754,584, incorporated herein by reference.

The following Examples 1-3 illustrate the preparation of inventive media containing or comprising a transition metal coating. The use of said coated media from Examples 1 and 2 with disclosed apparatus 100 (referenced below as a flow-through device) to reduce the concentration of two model malodor compounds from the airspace within a sealed test chamber is provided in Examples 4 and 5, below. The said coated media from Example 3 was used in a static sealed test chamber to reduce the concentration of a model compound in Example 6. Quantitative analytical results for these malodor reduction procedures are provided in Tables 1-3.

Examples 1-3

Preparation of Non-Woven Media Coated with Transition Metal Compound

Polyester fiber non-woven filter were cut using a circular die 4 inches in diameter. The non-woven filter (1.4 grams, weight accurately known, 4 inch diameter, 0.25 inch depth) were mounted vertically 5 inches in front of a pump sprayer containing a 1 weight % solution of Tyzor® TPT in isopropyl alcohol (Tyzor® TPT=99+% Ti(iso-propoxide)$_4$, E.I. du Pont de Nemours and Company, Wilmington, Del., USA). Six grams of the 1% Tyzor® solution was sprayed evenly onto both sides of the filter material. The filter material was allowed to air dry at 22° C. and approximately 60% relative humidity for at least 24 hours prior to use, thereby converting the Ti(iso-propoxide)$_4$ to hydrous titanium dioxide (DuPont Tyzor® Organic Titanates General Brochure). The filter material had a weight gain of approximately 20 mg, attributable to the hydrated titanium dioxide. The non-woven material had a noticeable white film deposited on the filter. The presence of hydrated titanium dioxide was confirmed by a visible color change to bright yellow upon exposure to hydrogen peroxide vapor.

Example 2 is the same as example 1, except that 5% Tyzor® solution was used in place of the 1% solution. The filter material has a weight gain of approximately 100 mg, attributable to the hydrated titanium dioxide.

Example 3 is the same as example 2, except that the circular non-woven filter was replaced with a rectangle of thin non-woven sheet measuring 4.5 inches by 3.5 inches. Two non-woven rectangle sheets were overlaid and sealed on 3 sides to create a pouch to which powder could be added later. The non-woven sheet had an approximate weight gain of 100 mg, attributed to the hydrated titanium dioxide.

Examples 4 and 5

Removal of Pentane Thiol Vapors in the Presence of Media Coated with Transition Metal Compound and Vapor Phase Hydrogen Peroxide, Using Flow Through Device Example 4: A 25 ft$^3$ sealed acrylic chamber was set-up to contain a mixing fan, hot plate, and flow through device having 2 filters and a vapor phase hydrogen peroxide source (a cylindrical filter paper dosed with 30 μl of a 50% aqueous hydrogen peroxide solution). The chamber atmosphere is interfaced with a gas chromatography apparatus ("Z-nose" 4100 Vapor Analysis System, Electronic Sensor Technology, Newbury Park, Calif., USA). The flow through device was set-up containing a blank (non-coated) non-woven filter, a cylindrical filter paper dosed with 30 μl of a 50% aqueous hydrogen peroxide solution, and the transition metal coated non-woven filter (prepared in example 1). Ten μl of an 8 wt % pentanethiol solution in methanol was added to the hot plate as the malodor. The malodor was volatilized by heating the hot plate for 10 minutes, using the mixing fan to quickly reach equilibrium within the sealed chamber. Analytical Z-nose date was recorded every 2.5 minutes throughout the course of the experiment. The experiment had three time regimes: 60 minutes of a static chamber followed by 60 minutes of the flow through device operating followed by an additional 60 minutes of static chamber. The static chamber readings allow for the determination of the natural removal of the malodor due to chamber sink effects and potential leak pathways which can then be accounted for in the flow through device regime. The analytical % malodor reduction was corrected for using the static region data. The analytical % reductions of the malodor in the test chamber airspace are provided in Table 1 for pentanethiol. Appropriate controls were also performed, and these results are included in Table 1 for comparison.

Example 5: same as Example 4, except using 5 μl of neat dibutylsulfide malodor liquid and transition metal coated non-woven filter prepared in Example 2. The analytical % reductions of the malodor in the test chamber airspace are provided in Table 2 for dibutylsulfide. Appropriate controls were also performed, and these results are included in Table 2 for comparison.

TABLE 1

Removal of Pentanethiol Vapors with Transition Metal Compound-Coated Filter in Combination with Vapor Phase Hydrogen Peroxide (VPHP)

| Flow-Through Device Set-up | % Reduction Experiment 1 | % Reduction Experiment 2 | Average % Reduction |
|---|---|---|---|
| Blank Filters Only | 4.58 | 5.63 | 5.11 |
| Blank Filters + VPHP | 35.79 | 29.94 | 32.87 |
| Tyzor Filter Only | 6.63 | 14.34 | 10.49 |
| Tyzor Filter + VPHP | 50.02 | 54.71 | 52.37 |

TABLE 2

Removal of Dibutylsulfide Vapors with Transition Metal Compound-Coated Filter in Combination with Vapor Phase Hydrogen Peroxide (VPHP)

| Flow-Through Device Set-up | % Reduction Experiment 1 | % Reduction Experiment 2 | Average % Reduction |
|---|---|---|---|
| Blank Filters Only | 4.63 | 10.44 | 7.54 |
| Blank Filters + VPHP | 12.16 | 13.27 | 12.72 |
| Tyzor Filter Only | 18.19 | 18.31 | 18.26 |
| Tyzor Filter + VPHP | 96.12 | 90.77 | 93.45 |

Example 6

Removal of Pentanethiol Vapors in the Presence of a Thin Non-Woven Media Coated with a Transition Metal Compound and Vapor Phase Hydrogen Peroxide, a Static Device Example 6: A 2.3 ft$^3$ acrylic chamber was set-up for experiments with the chamber atmosphere interfaced with a gas chromatography apparatus ("Z-nose"), similar to example 4. Within the acrylic chamber, a small weighing dish was position across the chamber from the Z-nose to hold the malodor solution and a low volume interior chamber was constructed to isolate the non-woven media from the chamber. 10 μl of a 0.8 wt % pentanethiol solution in methanol was added to the weighing dish as the malodor. The malodor was allowed to stabilize in the chamber for 10 minutes before sampling began. Analytical Z-nose data was recorded every 2.5 minutes throughout the course of the experiment. The experiment had three time regimes: 10 minutes of a static chamber for the malodor to evaporate and mix, followed by 60 minutes of recording the natural decay of the malodor in the chamber, followed by 60 minutes of the non-woven media exposed to the chamber. The only air flow within the chamber was generated by the Z-nose sampling pump during the course of the experiment. In experiments where the VPHP was used, a 10 μl dose of a 50% aqueous hydrogen peroxide solution was positioned within the interior chamber along with the non-woven media. The analytical % reduction was corrected for by subtracting the reduction in the background region. The analytical % reductions of the malodor in the test chamber airspace are provided in Table 3. Appropriate controls were also performed, and these results are also included in Table 3 for comparison.

TABLE 3

Removal of Pentanethiol vapors with a transition metal compound-coated non-woven in combination with vapor phase hydrogen peroxide (VPHP)

| Static Device Set-up | % Reduction Experiment 1 | % Reduction Experiment 2 | Average % Reduction |
|---|---|---|---|
| Blank Filters Only | 13.48 | 14.04 | 13.76 |
| Blank Filters + VPHP | 23.19 | 17.08 | 20.13 |
| Tyzor Filter Only | 26.57 | 36.07 | 31.32 |
| Tyzor Filter + VPHP | 57.33 | 60.75 | 59.04 |

The above data in Tables 1-3 illustrates the synergistic effect of the media coated with a transition metal compound when used in combination with vapor phase hydrogen peroxide as employed in the inventive flow through and static devices described herein.

While only certain embodiments have been set forth, alternatives and modification will be apparent from the above description to those skilled in the art. These and other alternatives are considered equivalents and within the scope of this disclosure and the appended claims.

The invention claimed is:

1. A method for reducing malodors in air, the method comprising:
   providing vapor phase hydrogen peroxide (VPHP); and
   engaging the malodors in the air and vapor phase hydrogen peroxide with a media comprising at least one transition metal element or a compound comprising a transition metal element, wherein the transition metal element is titanium.

2. The method of claim 1 wherein the exterior surface of the media further comprises at least one catalyst promoter comprising a salt comprising a non-transition metal cation and an anion selected from the group consisting of a halide, an oxide, a hydroxide, a carbonate, a sulfate, a silicate, an aluminate, a nitrate, a borate, a phosphate, a stannate, and a bismuthate.

3. The method of claim 1 wherein the transition metal compound is selected from the group consisting of titanium dioxide, titanium dioxide hydrates, and mixtures thereof.

4. The method of claim 1 wherein the VPHP is provided through passive evaporation of a composition comprising hydrogen peroxide.

5. The method of claim 1 wherein the VPHP is provided through sublimation of hydrogen peroxide from a solid composition comprising a hydrogen peroxide complex.

6. The method of claim 1 wherein the VPHP is provided by sublimation of hydrogen peroxide from a solid composition including at least one peroxohydrate compound.

7. The method of claim 6 wherein the solid composition comprises from about 0.1 to about 50 wt % hydrogen peroxide.

8. The method of claim 6 wherein the peroxohydrate compound is selected from the group consisting of urea peroxohydrate, sodium sulfate peroxohydrate, a peroxohydrate of poly (vinyl pyrrolidone) polymer and mixtures thereof.

9. The method of claim 6 wherein the solid composition is a powder, granule, compressed tablet or crystalline solid form.

10. The method of claim 6 wherein the solid composition further comprises one or more of fragrances, colorants, surfactants, solvents, binders, processing agents and hydrogen peroxide-stabilizing agents.

11. The method of claim 1 further comprising providing an air stream to increase engagement of the malodorous air and VPHP with the media.

12. An apparatus for treating malodors in air, the apparatus comprising:
a vapor phase hydrogen peroxide (VPHP) generator,
a media comprising a transition metal element or a compound comprising a transition metal element, wherein the transition metal element is titanium, an outer surface of the media being exposed to air and malodors in the air, the VPHP generator being positioned with respect to the media so that VPHP engages the media while in presence of the air and the malodors.

13. The apparatus of claim 12 further comprising an air movement mechanism to increase contact with the air, the malodors and the VPHP with the media.

14. The apparatus of claim 12 wherein the media is porous.

15. The apparatus of claim 12 wherein the media is a porous filter media coated with the transition metal element or the compound comprising the transition metal element.

16. The apparatus of claim 12 further comprising an air movement mechanism to increase contact between the air, the malodors in the air, the VPHP and the media.

17. The apparatus of claim 15 wherein the VPHP generator comprises a solid particulate peroxohydrate compound disposed within the porous filter media.

18. The apparatus of claim 12, wherein the VPHP generator comprises a reservoir of a hydrogen peroxide solution disposed in close proximity to the media.

19. The apparatus of claim 12 wherein the VPHP generator comprises a solid particulate peroxohydrate compound disposed within a porous container disposed opposite the media from an air displacement mechanism, and
wherein the air displacement mechanism draws an air stream past the porous container, across the media and past the air displacement mechanism.

20. The apparatus of claim 19 wherein the apparatus further comprises a vented base disposed opposite the air displacement mechanism from the media, the vented base comprising at least one vent opening through which the air stream passes after the air stream has passed through the porous container, across the media and past the air displacement mechanism.

21. A disposable device for treating malodors in air that includes one or more color change indicators for denoting device functionality, the device comprising:
a source of vapor phase hydrogen peroxide (VPHP),
a media comprising a titanium compound, and at least one chemical mechanism involving a prominent color change in a presence of VPHP.

22. The device of claim 21 wherein the at least one chemical mechanism involves
at least one transition metal compound which changes color in the presence of VPHP.

23. The device of claim 21 wherein the at least one chemical mechanism involves
at least one organic indicator compound which changes color in the presence of VPHP.

* * * * *